United States Patent
Leoncino et al.

(10) Patent No.: US 10,416,003 B2
(45) Date of Patent: Sep. 17, 2019

(54) RESONATING MEASUREMENT SYSTEM USING IMPROVED RESOLUTION

(71) Applicant: COMMISSARIAT A L'ENERGIE ATOMIQUE ET AUX ENERGIES ALTERNATIVES, Paris (FR)

(72) Inventors: Luca Leoncino, Grenoble (FR); Sebastien Hentz, Seyssinet-Pariset (FR); Guillaume Jourdan, Grenoble (FR); Marc Sansa Perna, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 85 days.

(21) Appl. No.: 15/499,292

(22) Filed: Apr. 27, 2017

(65) Prior Publication Data

US 2017/0314973 A1 Nov. 2, 2017

(30) Foreign Application Priority Data

Apr. 29, 2016 (FR) .................................. 16 53901

(51) Int. Cl.
  *G01D 5/353* (2006.01)
  *G01L 9/00* (2006.01)
  (Continued)

(52) U.S. Cl.
  CPC .............. *G01D 5/353* (2013.01); *G01D 5/26* (2013.01); *G01D 5/34* (2013.01); *G01L 1/103* (2013.01);
  (Continued)

(58) Field of Classification Search
  CPC combination set(s) only.
  See application file for complete search history.

(56) References Cited

U.S. PATENT DOCUMENTS

2009/0238515 A1  9/2009 Fattal et al.
2014/0283601 A1* 9/2014 Bhave .................. G01P 15/093
                                      73/504.12

FOREIGN PATENT DOCUMENTS

AU    2016200064 A1   1/2016
WO  WO 2005/081929 A2   9/2005
WO  WO 2012/113034 A1   8/2012

OTHER PUBLICATIONS

French Preliminary Search Report dated Jan. 24, 2017 in French Application 16 53901 filed on Apr. 29, 2016 (with English Translation of Categories of Cited Documents).

(Continued)

*Primary Examiner* — Tony Ko (74) *Attorney, Agent, or Firm* — Oblon, McClelland, Maier & Neustadt, L.L.P.

(57) ABSTRACT

A resonating measurement system having at least a microelectromechanical system (MEMS) and/or nanoelectromechanical system (NEMS) is provided, including an optomechanical device comprising at least one resonating element at at least one resonance frequency of fr, and at least one optical element having an optical index sensitive to displacement of the at least one resonating elementl; excitation circuitry configured to excite the at least one resonating element at at least at one operating frequency of fm; an injection device configured to inject a light beam, having an intensity modulated at frequency of $f1=fm+\Delta f$, in the optomechanical device; and a photodetection device configured to measure an intensity of a light beam transmitted from the optomechanical device, the intensity having at least one component at frequency of $\Delta f$.

19 Claims, 3 Drawing Sheets

(51) Int. Cl.
*G01P 15/093* (2006.01)
*G01P 15/097* (2006.01)
*G01D 5/26* (2006.01)
*G01D 5/34* (2006.01)
*G01M 11/00* (2006.01)
*G01N 29/036* (2006.01)
*G01N 29/24* (2006.01)
*G01L 1/10* (2006.01)

(52) U.S. Cl.
CPC ....... *G01L 9/0023* (2013.01); *G01M 11/3172* (2013.01); *G01N 29/036* (2013.01); *G01N 29/2418* (2013.01); *G01P 15/093* (2013.01); *G01P 15/097* (2013.01); *G01N 2291/015* (2013.01); *G01N 2291/0256* (2013.01); *G01N 2291/0427* (2013.01)

(56) References Cited

OTHER PUBLICATIONS

I. Bargatin et al. "Sensitive detection of nanomechanical motion using piezoresistive signal downmixing," Applied Physics Letters 86, 133109, 2005, pp. 3.

Ivan Favero, "Gallium Arsenide Disks as Optomechanical Resonators," Cavity Optomechanics, Quantum Science and Technology, 10. I 007/978-3-642-55312-7 _7, 2014, pp. 8.

Jonathan Lee et al. "High-Q silicon carbide photonic-crystal cavities", Applied Physics Letters 106, http://dx.doi.org/10.1063/1.4906923 041106, 2015, pp. 4.

* cited by examiner

RESONATING MEASUREMENT SYSTEM USING IMPROVED RESOLUTION

TECHNICAL DOMAIN AND PRIOR STATE OF THE ART

This invention relates to a measurement system implementing resonating MicroElectroMechanical Systems (MEMS) and/or NanoElectroMechanical Systems (NEMS), which can for example be used for gas analysis, mass spectrometry for the detection of chemical or biological species, as force sensors or inertial systems, such as a resonating accelerometer, gyrometer, or pressure sensor.

A resonating sensor has a mechanical resonator put in vibration at its resonance frequency by excitation means. The resonator resonance frequency varies depending on environmental parameters; by measuring the resonance frequency variation, it is possible to determine the parameter(s) having modified the mechanical resonator resonance frequency. The resonator is for example a beam suspended on a fixed part, the beam being put in vibration at its resonance frequency by capacitive means. For example, particles depositing on the beam cause a shift in the resonance frequency, the amplitude of this shift is related to the mass of the material deposited.

The displacement of the beam is for example detected by piezoelectric means typically comprised of two strain gauges mounted differentially, the gauges being suspended between the beam and the fixed part.

The resolution of such a sensor is determined by its sensitivity, i.e. the relationship between the resonance frequency and the parameter measured, and the frequency stability, i.e. the minimum variation of the resonance frequency.

The sensitivity to mass of the sensor may be written as:

$$S = \frac{\Delta f}{\Delta m} = \frac{f_r}{2M}$$

$\Delta m$ is the variation of mass on the mobile part of the sensor, $\Delta f$ is the variation in measured frequency resulting from the variation in mass, $f_r$ is the mobile part resonance frequency and M is the mobile part mass.

In addition, the resolution in resonance frequency is inversely proportional to the signal to noise ratio (SNR) and the quality factor Q. It may be written as:

$$\Delta f_r = \frac{f_r}{2QSNR},$$

The mass resolution $\Delta m$ is then given by:

$$\Delta m = \frac{M}{QSNR}.$$

It appears therefore that, to maximize the mass resolution, it is desirable on one hand to reduce the mass M of the mobile part and that it presents high resonance frequencies, and on the other hand to have transduction means offering a significant SNR.

By reducing the dimensions of the mobile part, we obtain both a reduction of its mass and an increase in the resonance frequency, which allows to improve the mass resolution and sensitivity to mass. But this reduction of size imposes to detect a movement to more high frequencies.

In addition, the variation of resonance frequency may not result only as a result of the mass of particles deposited on the mobile part but also the location of the deposit of particles on the mobile part and the size of the particles. In order to achieve a detection that allows distinguishing the effects of the mass and for example the location of the deposit and/or the size of the particles deposited, it is useful to combine the information obtained by working in different modes of resonance frequencies. However, a detection in higher order modes involves working at still higher frequencies.

However, the detection at very high frequencies has some drawbacks.

The piezoresistive and capacitive means of detection do not perform well when the frequencies are greater than a few hundred MHz. Short-circuits appear between the electrical elements participating in the detection, resulting in parasite capacities. These parasite capacities coupled with resistances of the NEMS generate the appearance of a low-pass filter which therefore prevents the detection at high frequencies.

The document I. Bargatin, E. B. Myers, J. Annica Annika, B. Gudlewski, and M. L. Roukes, "*Sensitive detection of nanomechanical motion using signal piezoresistive down mixing,*" Phys. Appl. Lett., vol. 86, no. 133109, 2005 describes a method for the detection of high frequency MEMS resonators using nano-strain gauges. This method is designated "down mixing". It consists of polarizing the strain gauges with a signal at a frequency $f_r+\Delta f$ while the beam is actuated at frequency $f_r$.

The output mechanical signal has then a component at $\Delta f$, the value of $\Delta f$ is chosen less than the low-pass filter cut-off frequency generated by the short-circuits mentioned above.

This method therefore allows a high frequency detection using piezoresistive means.

In addition, the mode of operation by down mixing allows reducing the measurement background which is a parasite signal at the same frequency as the mechanical signal and which is superimposed on the latter. In effect, the excitation circuit and the measurement circuit are generally coupled to one another for example in a capacitive, inductive or common impedance manner. A crosstalk phenomenon between the excitation signal and the measuring signal may appear. Since the excitation frequency signal is at f and that of the measuring signal is at $\Delta f$ by the down mixing method, it is possible to eliminate by frequency filtering the measurement background of the mechanical measurement signal.

However, the inventors have determined that despite the application of the down mixing method, there still existed a measurement background at the detection frequency $\Delta f$.

In addition, the frequency of the polarization signal is generally limited to approximately 300 MHz; beyond this frequency, it becomes complex to polarize the strain gauges effectively. There is an impedance discontinuity between the propagation line that is typically of the order of 50 Ω and the impedance of the gauge(s) that is in practice several thousands of Ohms. This impedance discontinuity can greatly reduce the bias current at the level of the gauges that control the electromechanical signal. There is then a reduction in the sensitivity. This has the effect of reducing the SNR of the resonator signal and thus reduces the resolution of the resonator's resonance frequency variation measurement.

DISCLOSURE OF THE INVENTION

It is therefore a purpose of this invention to offer an MEMS and/or NEMS resonating measurement system that offers a high resolution and presents a reduced measurement background in comparison with the resonating measurement systems of the state of the art.

The inventors have determined that the measurement background which subsisted was the result of the modulation of the resistance value of the strain gauges due to the temperature variation due to the heating by Joule effect resulting from the current circulation in the gauges induced by the actuation circuit. They then thought to achieve a resonating MEMS and/or NEMS measurement system containing at least one mobile part forming a resonator fit to be put in vibration by a force at frequency fm, an actuation frequency which produces a mechanical movement at this same frequency, by excitation means and detection means, implementing optical detection means with a light source of which the intensity is modulated at a frequency fm+Δf and an optomechanical device whose optical transmission function, which is at least in part modified by the displacement of the mobile part and the means of photodetection measuring the intensity of the signal transmitted by the optomechanical device. Δf can be either positive or negative.

Thus, while using optomechanical detection means, by injecting a light beam whose amplitude is modulated in frequency fm+Δf, and by exciting the resonator at frequency fm, the measurement background is greatly reduced, both the one resulting from the crosstalk and the one resulting from the heating by Joule effect In addition, the embodiment of optical detection means allows to overcome the problems of parasite capacities generating a low-pass filter, and to be free, in the case of a sensor operating according to the down mixing method, of the impedance discontinuity in the measuring circuit and therefore the gauge polarization problems.

For example, the actuation is achieved in a capacitive manner or by means of an optical beam. In the case of actuation by an optical beam, it may be advantageous to use an optical beam whose wavelength is different from that of the measurement beam, in order to maximize forces generated by the optical beam. For example, we may choose a frequency that corresponds to a resonance sufficiently far removed from that used for the detection, which can eliminate the actuation light beam in the photodetector.

In an advantageous manner, the fr/Δf ratio is greater than or equal to 10.

The resonating element can be a beam or a membrane. As a variation, it could be formed directly by the optical element, as a portion of the wave guide that would be suspended or by an optical ring also suspended.

In an advantageous manner, the mobile part is related to the electrical ground which allows further reducing the self-heating.

The subject-matter of this invention is therefore a resonating measurement system having at least MEMS and/or NEMS, comprising:
- an optomechanical device comprising at least one resonating element at at least one resonance frequency of fr and at least one optical element whose optical index is sensitive to the displacement of the resonating element,
- excitation circuitry of exciting the resonating element at least at one operating frequency of fm,
- injection device for injecting a light beam whose intensity is modulated at frequency f1=fm+Δf in the optomechanical device,
- a photodetection device configured measure the intensity of a light beam coming out of the optomechanical device, the intensity of the measurement beam having at least one component at frequency Δf.

BRIEF DESCRIPTION OF THE DRAWINGS

This invention will be better understood based on the description that will follow and the annexed drawings on which.

DETAILED DESCRIPTION OF THE INDIVIDUAL EMBODIMENTS

Figure 1:
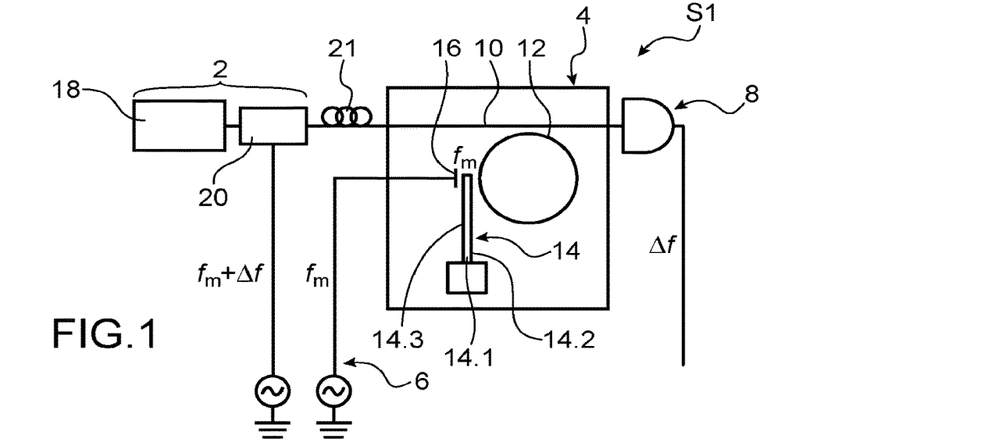
FIG. 1 is a schematic representation of an example of the embodiment of a resonating measurement system according to this invention in which the resonating element is a suspended beam.

In FIG. 1, we can see a schematic representation of an S1 resonating measurement system according to the invention.

The measuring system includes generation means of a light beam 2, an optomechanical device 4, optomechanical device mobile element excitation means 6 and at least one photodetector device 8.

In the example shown, the optomechanical device 4 is comprised of a wave guide 10 in which the light beam emitted by the generation means 2 is injected, an optical ring 12 in the vicinity of the wave guide 10 so that the wave guide can inject the incident light beam into the optical ring 12 and collect the light beam transmitted or reflected by the optical ring 12.

The optomechanical device 4 also includes a mobile element 14 able to be put in vibration at a particular frequency or its resonance frequency and positioned in the vicinity of the optical ring so that the displacement of the mobile element 14 causes a change of the effective optical index of the optical ring 12 in disturbing its evanescent field.

In the example shown, the mobile element 14 is a mobile beam built-in by a longitudinal extremity 14.1 in a fixed part of the system. The beam 14 is positioned so that a side edge 14.2 faces to the outer periphery of the optical ring 12 and so that it is able to be moved in the optical ring 12 plane. As a variant, the mobile element 14 is a membrane or a non-deformable mass in any form, for example rectangular, which vibrates in the plane and whose air gap with the optical resonator varies.

The elements of the optomechanical device can be in the open air or be encapsulated within a controlled environment, for example under vacuum.

According to another example, the optomechanical device is comprised of two wave guides positioned on either side of the ring, one used for the injection of the light beam emitted by the means 2 and the other used to collect the outgoing light beam exiting the wave guide. As a variant, the two wave guides could collect the light beam exiting the optical ring.

In another example, the device has a wave guide and a resonator for example a beam, the displacement of the beam directly influencing the wave guide optical index.

The optical ring could be replaced by any other optomechanical structure. For example, the optical ring could be replaced by any optomechanical structure, for example a disk as this is described in the document *Favero I., gallium arsenide disks as Optomechanical resonators, In: Aspelmeyer M, Kippenberg T J, Marquardt F, publishers. Cavity Optomechanics* 2014. p. 149-156. *Quantum Science and Technology*—DOI10.1007/978-3-642-55312-7_7. As another variant, the ring is replaced by a nanobeam cavity, such as that described in the document *Lee J Y, Lu X, Lin Q. High-Q silicon carbide photonic-crystal cavities. Applied Physics Letters*. Jan. 26, 2015; 106(4):041106.

The means for setting the mobile element 14 in motion are in the electrostatic type example represented and include an electrode 16 facing another side edge 14.3 of the beam opposite the side edge 14.2 facing to the optical ring 12. When power is applied to the electrode 16, an electrostatic force is applied on the beam 14 which is then put in motion. By applying a periodic excitation signal, the beam is put in vibration. The excitation means 6 are configured to put the mobile element in motion at least at a frequency fm close to the resonance frequency fr of the mobile element 14. Preferably, fm is chosen such that fr−(2fr/Qm)≤fm≤fr+(2fr/Qm), with Qm the mobile element 14 mechanical quality factor.

fm is chosen as a working frequency at which one wants to measure the mechanical system response x(fm) (for example in the spectral domain, x(fm) is proportional to the transfer function H, x=H F, F is the force modulated at fm) And advantageously, fm is equal to fr to measure the mechanical system response of the frequency where the amplitude response is maximum.

The electrical signal may have a frequency fm or fm/2 because the force generated is proportional to the voltage squared.

As a variant, the initiation of vibration of the mobile element 14 is obtained by using the optical actuation means, for example a pumping light beam at frequency fr. Preferably an actuation beam whose wavelength is different from that of the detection light beam is used, which allows to filter this optical signal which is a competitor to the detection signal at the photodiode. By filtering this signal, a reduction in the measurement background can thus be obtained allowing the achievement of better background signal ratios.

The optomechanical device then presents as a function of optical transmission T(x, λ), x being in a position of the mechanical system and λ being the wavelength of the entering light beam.

In the first order in displacement x, $T=T_0(\lambda)(1+\alpha(\lambda)x)$.

The means of generation of a light beam includes a light source, advantageously a laser source, comprising a laser diode 18 and modulation means 20 so that the intensity of the light beam penetrating in the wave guide is a frequency fm+Δf.

The modulation means 20 may directly modulate the supply current of the laser diode.

In an advantageous manner, the modulation means 20 include advantageously an electro-optic modulator interposed between the laser source and the optomechanical device, which modulates the intensity of the laser beam. The electro-optical modulator allows advantageously to increase the frequency and to benefit from a greater modulation range. In effect, an optomechanical modulator allows to reach frequencies of at least 40 GHz, whereas the modulation of the current of the laser diode is limited in frequency, typically a few hundred MHz.

In addition, the diode supply current modulation amplitude is limited by the fact that the response between the laser power and the supply current is non-linear and by the fact that the diode supply current must be higher than a threshold current to ensure the laser regime for the diode.

The light beam emitted by the electro-optic modulator has an intensity which can be written as $I=I_0+M\ I_0 \cos((f_r+\Delta f)t)$.

A polarization controller 21 may be provided upstream of the wave guide 10 in the case where the optical transmission function of the entire system is sensitive to the polarization, which allows to optimize the optomechanical coupling. For example in the case of the optical ring, a transverse electrical polarization can maximize the optomechanical coupling.

The modulated light beam is sent in one extremity of the wave guide 10. The photodetection device is positioned facing the other end of the wave guide. The photodetection device includes for example at least one photodetector which measures the light signal transmitted or reflected.

The detected signal includes a component at a frequency Δf and a component at a frequency $2f_r+\Delta f$. If the component in 2fr+Δf is in the photodetector bandwidth, a low-pass filter is provided to remove this component. If the component in 2fr+Δf is outside the photodetector bandwidth, a low-pass filter is not required to remove this component.

The operation of the measurement system in FIG. 1 will now be described in an application upon detecting the deposit of particles.

The beam 14 is set in vibration under the effect of an actuation force at frequency fm. The displacement of the beam has an effect on the effective optical index of the optical ring 12.

A light beam with a modulated intensity at frequency fm+Δf is injected into the wave guide 10.

The light beam circulates in the optical ring 12. A detection light beam is collected by the wave guide 10.

When one or more particles are deposited on the beams, their mass varies, causing a variation of its resonance frequency. This resonance frequency modification will modify the effective optical ring optical index. The optical transmission function T is modified, the optical beam modified is collected by the wave guide 10 and then by the photodetection device.

The output signal combines two signals: the modulated intensity of the light beam and the modulation due to the displacement of the beam.

Figure 5:
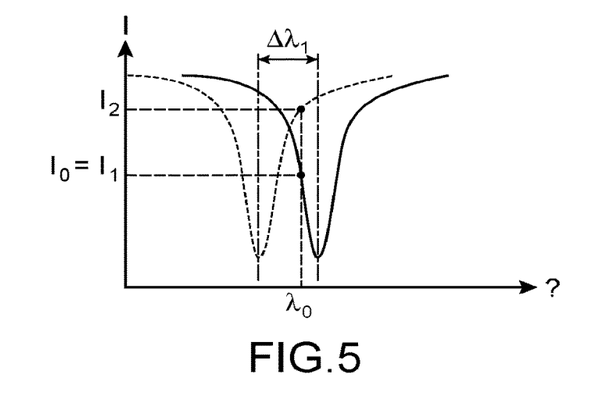
FIG. 5 is an example of two optical spectra obtained with a system according to the invention, representing a variation of the amplitude of the light signal measured by the photodetector as a function of the wavelength and for two different positions generating a shift Δλ of the optical resonance peak.

In FIG. 5, you can see an example of an optical spectrum that can be obtained with the measurement system according to the invention. In this representation, this is wavelength λ and not the frequency. When the resonator is excited, it moves between two positions 1 and 2. As a full line, it is the measurement of the intensity I equal to $I_1$ for the position 1 of the resonator, and as a dashed line, it is for example the measure of the intensity I equal to $I_2$ for position 2 of the resonator. In the absence of particles, the resonator oscillates at a certain speed between these two positions. When particles settle on the resonator, a variation of the resonance frequency of the resonator mechanical appears, which changes the resonator oscillation speed between the two positions and thus the speed of the offset of the optical spectrum. The variation of the speed of this offset is representative at least in part of the mass deposited on the resonator.

The mechanical displacement is transcribed to frequency $\Delta f$, for example 100 kHz.

The amplitude of the output signal picked up by the photodetector is the following:

$$I_{PD} = I \times T_0(\lambda)(1+\alpha x)$$

For a movement $x = x(f_m)\cos(2\pi f_m t)$, by keeping only the proportional part to the displacement x by depositing some $s = T_0 \alpha$.

$$I_{PD} = \left\{ \left[ (I_0 + I_0 M \cos[2\pi(fm + \Delta f)t]) \right] \cdot sx(fm) \cdot \cos(2\pi fmt) = \right.$$
$$\left. sx(fm)I_0 \left\{ \cos(2\pi fmt) + \frac{M}{2}[\cos(4\pi fmt) + \cos(2\pi \Delta ft)] \right\} \right.$$

The component at $\Delta f$ of the intensity of the light beam detected $I_{d,\Delta f}$ is therefore:

$$I_{d,\Delta f} = \frac{M}{2} sx(f_m) I_0 \cos(2\pi \Delta f t).$$

s is the optomechanical transduction factor. x(fm) is the amplitude of the mechanical response of the beam at frequency fm.

The measurement system according to the invention allows therefore to operate at a frequency smaller than fm, the resolution of the system can therefore be improved.

In addition, by distinguishing the excitation frequency from the output signal frequency, the measurement background due to the crosstalk is reduced.

Figure 6:
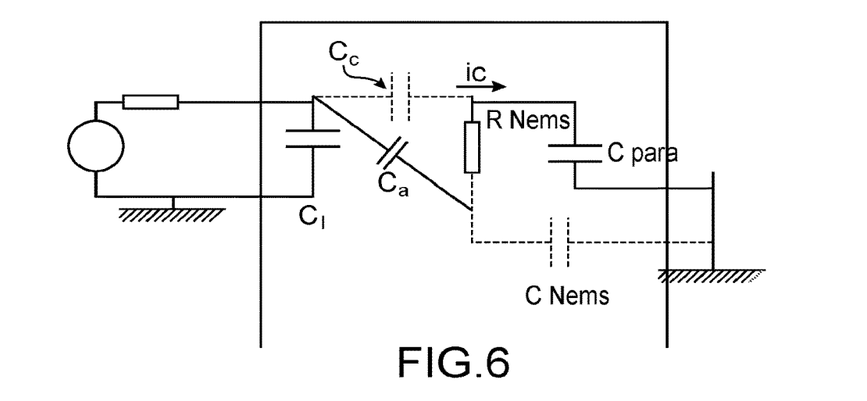
FIG. 6 is a schematic representation of the electric coupling appearing between the excitation means and the mechanical part and between the mechanical part and the mass in an example of embodiment of a system according to the invention.

In addition, the background signal due to the self-heating is reduced significantly. The electrical diagram illustrating the coupling and the coupling current circulation is represented in FIG. 6.

Cc represents the parasite capacity between the actuation electrode and the electrical leads connected to the beam, Rnems represents the beam 14 resistance or impedance or more generally of the mechanical part, Ca represents the coupling capacity between the excitation means and the mechanical part. We have Ca«Cc. The capacity of the Ca coupling serves as a capacitive actuation. This is a capacity specific to the excitation circuit.

Cpara represents the parasite capacity appearing between the electrical ground and the electrical access leads and Cnems represent the capacity that appears between the mechanical part and the ground.

ic is the coupling current which appears from the fact of the coupling of Ca and Cc between the excitation means and the mechanical part, coupling mainly between the access leads of the excitation means and the mechanical part (Cc). The Cpara capacity being much greater than the Cnems capacity, its impedance is lower than that of the Cnems capacity; the coupling current then flows to the electrical ground through a parasitic capacitance between the access leads and the ground (Cpara) and not through the mechanical part and the electrical ground (Cnems). The heating due to the Joule effect is therefore significantly reduced compared to state of the art systems because of the absence of current passing through the NEMS resistor.

ic is flows mainly through the Cpara capacity toward the electrical ground.

Figure 7:
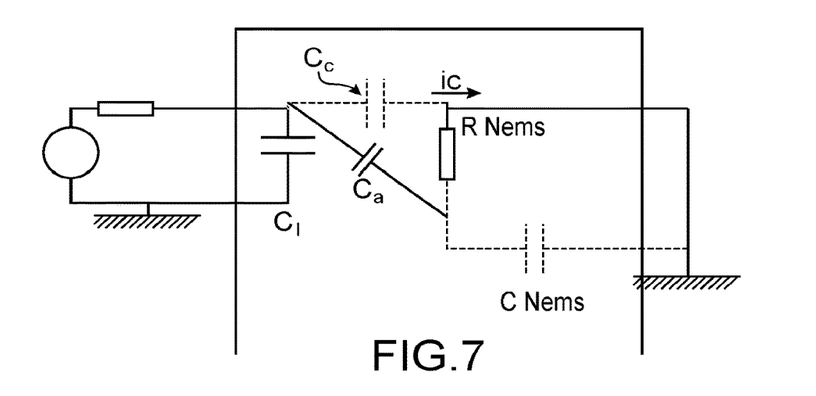
FIG. 7 is a schematic representation of the electric coupling appearing between the excitation means and the mechanical part and between the mechanical part and the mass in an example of embodiment of a system according to the invention.

In an advantageous manner, the mechanical part symbolized by the Rnems impedance is connected directly to the ground. Then there is no Cpara parasite capacity. The self-heating is further reduced because all the current flows through this short-circuit.

The electrical diagram illustrating the coupling and the coupling current circulation is represented in FIG. 7.

Moreover, by choosing a sufficiently low $\Delta f$, this component can advantageously be detected by a low bandwidth photodetector and having a low Noise Equivalent Power (NEP). In addition, a common low frequency electronic such as an LIA can be used, which allows detecting the resonator phase, from which a consistent actuation of an inconsistent actuation can be distinguish and also work in a Phase Lock Loop mode (PLL).

It is to be noted that the M/2 factor does not imply a loss of performance because the noise upstream of the photodiode, for example the thermomechanical noise is mitigated in the same manner. The SNR is therefore preserved.

Preferably, the value of $\Delta f$ is chosen in order to be above the measurement bandwidth set by the mechanical resonator $$\frac{f_r}{Qm}.$$

In addition, $\Delta f$ is chosen lower than the photodetector bandwidth.

Preferably, the $f_r/\Delta f$ ratio is then greater than or equal to 10, which allows to have a good compromise between the bandwidth needs and the reduction needs of the measurement frequency. For example, for a 100 MHz resonator with a quality factor Qm=10,000, it is desirable to arrange $\Delta f>10$ kHz which allows to benefit from the entire bandwidth of the resonator. Preferably at $\Delta f>100$ kHz, a frequency is chose such as the electronics has a lower noise.

Advantageously, $1 < f_r/\Delta f < Qm$, and in a preferred manner $10 < f_r/\Delta f < Qm/5$.

In an advantageous manner, the invention allows performing the measurements at other resonator resonance frequencies and thus to make the measurements to several mechanical modes, in particular of the mechanical modes of superior orders, while retaining a good resolution. We can predict advantageously to repeat measurements at different resonance frequencies in order to obtain more information on the deposited particles, such as their size and location and obtain a more complete result on the nature or the mass of the particles.

In the case of a gravimetric measuring system for example for the detection of gas, the molecules adsorbed are desorbed for example by heating the resonator.

Figure 2A:
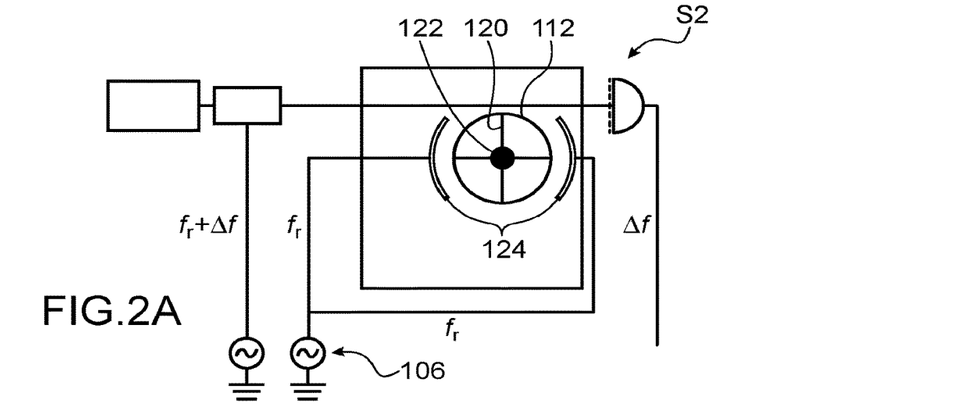
FIG. 2A is a schematic representation of an example of the embodiment of a resonating measurement system according to this invention in which the mobile element is formed directly by an optical component.

In FIG. 2a, we can see another example of embodiment S of a measuring system according to the invention. System S differs from the system S in the fact that the optomechanical device directly uses as vibrant element the optical ring.

Optical ring 112 is maintained on the bracket using spokes 120 linked to a fastener 122 to the bracket at the centre of the ring.

Figure 2B:
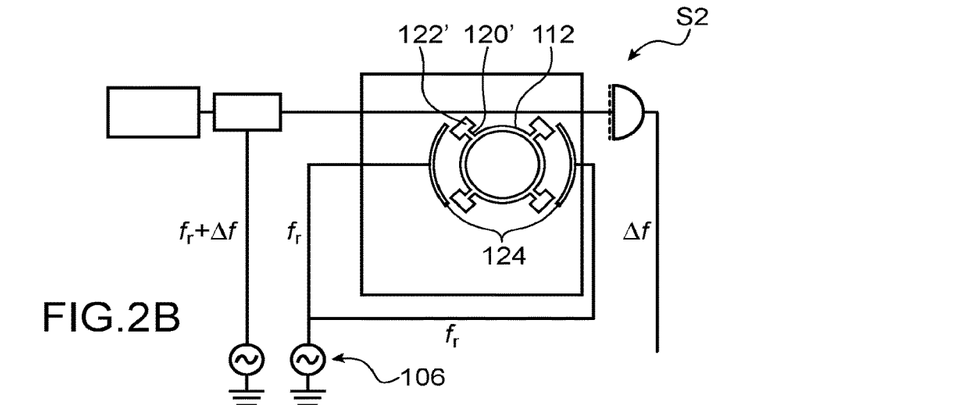
FIG. 2B is a schematic representation of another example of embodiment of a resonating measurement system according this invention, in which the mobile element is formed directly by an optical component.

In FIG. 2B, we can see another example of embodiment in which the optical ring is maintained by outer radii 120' anchored on the bracket by pads 122'.

The excitation means include electrodes 124, in the form of an arc of a circle, facing the outer edge of the ring. The electrodes are for example fixed to the bracket. In the example shown, the excitation means 106 includes two diametrically opposed electrodes. When the excitation means are activated, diametrically opposed forces are applied to the optical ring 112 which deforms radially and "breathes". The optical ring then directly forms the resonator.

In another example, the wave guide can be directly used as resonator, at least a part of the wave guide being able to be put in vibration by the excitation means.

The operation of system S is close to the functioning of system S1, it differs in that the particles settle directly on the optical ring, which causes a change of its resonance frequency fr2, the optical index is then modulated at the new resonance frequency fr2, whereas prior to the deposit of particles the effective index optical was modulated to fr1. The effect on the amplitude of the luminous flow injected at fm+Δf is therefore modified.

Figure 3:
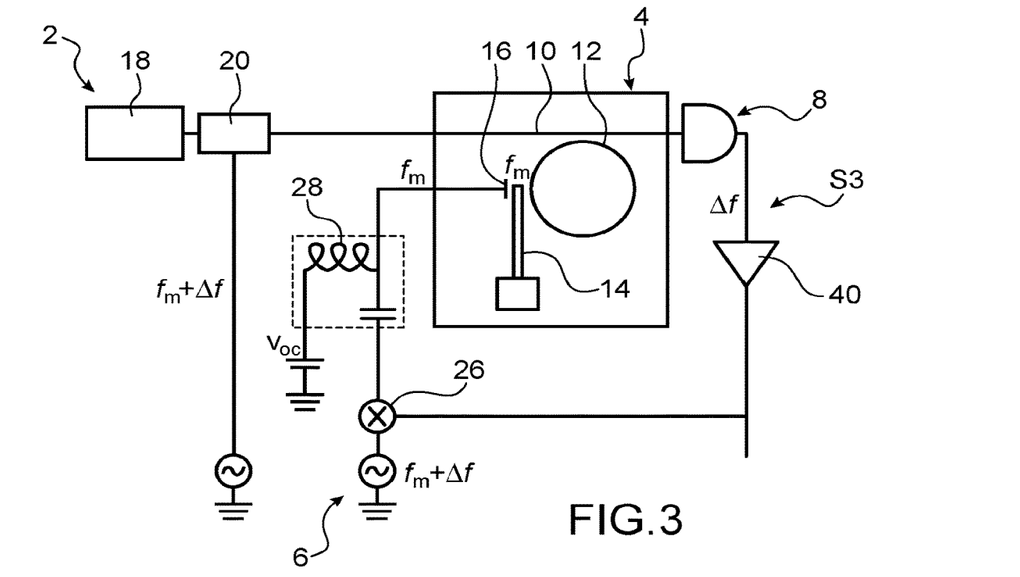
FIGS. 3 and 4 are schematic representations of two examples of embodiment of a self-oscillating resonating measurement system according to this invention.
Figure 4:
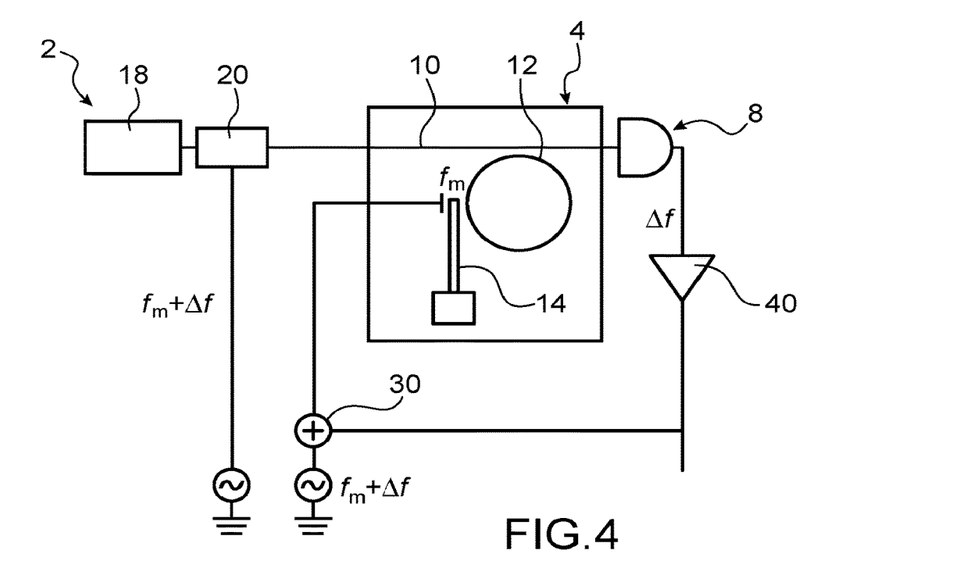

On FIGS. 3 and 4, we can see examples of measurement systems according to the self-oscillating invention.

In FIG. 3, system S3 contains the elements of system S1 and means 26 to mix the photodetector device output signal at frequency Δf with an actuation signal at fm+Δf, for example, by multiplying the sinusoidal signals at Δf and fm+Δf in a way to generate a signal at fm. This signal to which a continuous $V_{DC}$ signal is added by means a bias T 28, is applied to the electrode putting the mobile element in vibration. By adjusting the phase and amplitude of the signal at fm+Δf, the self-oscillation conditions can be reached. In an advantageous manner, a component 40 such as an amplifier or a filter downstream of the photodiode ensures the conditioning of the photodiode output signal, i.e. it eliminates parasite signals, and ensures an amplification gain allowing self-oscillation conditions.

In FIG. 4, system S4 contains the elements of system S1 and means 30 adding the output signal of the photodetector device at the frequency Δf and an actuation signal at fm+Δf.

By adjusting the signal phase and amplitude at fm+Δf, self-oscillation conditions can be reached.

As for system S3, in an advantageous manner, a component 40 such as an amplifier 40 or a filter downstream of the photodiode ensures the conditioning of the photodiode signal output, i.e. it eliminates parasitic signals, and ensures an amplification gain allowing self-oscillation conditions.

The system can advantageously continuously assess the actual mechanical system resonance frequency and adapt itself by using this value. Indeed, the resonance frequency may vary over time, for example as a function of external elements when the particles are deposited or during their desorption.

As has already been mentioned, the resonating measurement system according to the invention allows reducing the measurement background in the output signal and maintaining high sensitivity and resolution.

In addition, since the measurement system output signal according to the invention obtained by a photodetector has a component in Δf, it is possible to use a photodetector operating at low frequency and with a low bandwidth that has a significantly lower cost than wide bandwidth photodetectors. With a low bandwidth photodetector, even the high frequency modes outside the photodetector bandwidth are accessible because it is the Δf value which intervenes. It is then advantageously possible to perform a detection in different modes and to obtain more complete information on the particles deposited in the case of the detection of particles.

In addition, the fact of being able to use a low frequency photodetector contributes to improve the SNR because the input noise of such a photodetector is lower than that of high frequency photodetectors. Moreover, these photodetectors present a high gain, they thus have an electrical signal easily read from a measuring instrument without adding Voltage Noise Density from the LIA(Lock In Amplifier) or an oscilloscope. Moreover, when operating at low frequency, a synchronous detection amplifier or LIA can be used to also measure the resonator phase, which allows for example to distinguish consistent actuations from inconsistent actuation (Brownian noise). In addition, the fact of having the phase allows working in phase-locked loop mode.

In addition, the invention avoids the electrical polarization control problems due to impedance discontinuities and allows an effective modulation of the signal used to measure.

In addition, since the output signal is at frequency Δf which is chosen low, a low frequency electronics, for example operating between 1 MHz and 10 MHz may be sufficient for the analogue processing, digitization and all the elements of the information processing chain. We thus gain in terms of the energy consumption and ASIC space necessary for portable, autonomous systems or which require a high miniaturization.

The system according to the invention may be manufactured using integrated circuit manufacturing technologies. It is adapted for integration into Very Large Scale Integration (VLSI).

For example, the device is manufactured from a Silicon On Insulator plate (SOI). The silicon upper layer can be etched using photolithography to embody the geometry of the ring, the wave guide and the resonating beam. Then, a partial etching of the buried oxide is implemented to release the beam. The integration of the laser on the substrate, modulator, and photodetector can for example be embodied by media transfer techniques.

The measurement system is particularly suitable for applications requiring both high frequency and sensitivity. The application to the measurement of particulate mass for example in the mass sensors has been described more precisely, but it can be applied to achieve the inertial sensors such as resonating accelerometers, gyrometres, in an atomic force microscope. . .

The invention claimed is:

1. A resonating measurement system having at least a microelectromechanical system (MEMS) and/or a nanoelectromechanical system (NEMS), comprising:
    an optomechanical device comprising at least one resonating element at at least one resonance frequency of fr, and at least one optical element having an optical index sensitive to displacement of the at least one resonating element;
    excitation circuitry configured to excite the at least one resonating element at at least at one operating frequency of fm;
    an injection device configured to inject a light beam, having an intensity modulated at a frequency of f1=fm+Δf, into the optomechanical device; and
    a photodetection device configured to measure an intensity of a light beam transmitted from the optomechanical device, the intensity having at least one component at a frequency of Δf.

2. The resonating measurement system according to claim 1, wherein the at least one operating frequency of fm is such that $fr-(2fr/Qm) \leq fm \leq fr+(2fr/Qm)$, where Qm is a mechanical quality factor of the at least one resonating element.

3. The resonating measurement system according to claim 2, wherein a ratio $fr/\Delta f$ is such that $10 < fr/\Delta f < Qm$.

4. The resonating measurement system according to claim 1, wherein the optomechanical device includes a wave guide and an optical ring optically coupled to the wave guide, the wave guide being configured to receive the light beam injected by the injection device and to send a transmitted light beam via the optomechanical device to the photodetection device.

5. The resonating measurement system according to claim 4, wherein the at least one resonating element is positioned in a vicinity of the optical ring.

6. The resonating measurement system according to claim 4, wherein the at least one resonating element is formed by the optical ring.

7. The resonating measurement system according to claim 1, wherein the excitation circuitry is an electrostatic excitation circuitry.

8. The resonating measurement system according to claim 1, wherein the excitation circuitry is an optical excitation circuitry.

9. The resonating measurement system according to claim 1, wherein the light beam transmitted from the optomechanical device also has a component at a frequency of $2fm+\Delta f$ and/or $fm+\Delta f$, the photodetection device comprising at least one photodetector having a bandwidth such that a component at the frequency $2fm+\Delta f$ and/or $fm+\Delta f$ is outside said bandwidth.

10. The resonating measurement system according to claim 1, wherein the photodetection device has at least one photodetector and a bandpass filter so that the light beam transmitted from the optomechanical device also has a component at a frequency of $2fm +\Delta f$ and/or $fm+\Delta f$ that is outside of a bandwidth of said bandpass filter.

11. The resonating measurement system according to claim 1, wherein the injection device comprises a light source formed by a laser.

12. The resonating measurement system according to claim 11, wherein the injection device includes modulation means of a laser supply current.

13. The resonating measurement system according to claim 11, wherein the injection device comprises a laser diode.

14. The resonating measurement system according to claim 1, wherein the injection device comprises a light source and an optical modulator positioned between the light source and the optomechanical device and is configured to modulate to a frequency of f1 the light beam injected into the optomechanical device.

15. The resonating measurement system according to claim 1, further comprising an electrical connection between the at least one resonating element and an electrical ground of the resonating measurement system.

16. The resonating measurement system according to claim 1, further comprising additional circuitry either disposed directly at an output of the photodetection device, or at the output of the photodetection device through a component, configured to generate a signal on based on a mixture of the component at the frequency of $\Delta f$ of a photodetection device output signal and a signal at the frequency of $f1=fm+\Delta f$, so as to generate a self-oscillating measurement system.

17. The resonating measurement system according to claim 16, wherein the additional circuitry is connected to the output of the photodetection device through an amplifier or a filter.

18. The resonating measurement system according to claim 1, further comprising additional circuitry disposed either in an output of the photodetection device through a component, configured to generate a signal corresponding to a sum of the component at the frequency of $\Delta f$ of a photodetection device output signal and a signal at the frequency of $f1=fm+\Delta f$, so as to generate a self-oscillating measurement system.

19. The resonating measurement system according to claim 18, wherein the additional circuitry is connected to the output of the photodetection device through an amplifier or a filter.

* * * * *